United States Patent [19]

Evans et al.

[11] 4,229,577

[45] Oct. 21, 1980

[54] YELLOW PHOTOGRAPHIC COLOR COUPLERS CONTAINING 3-IMINO-1,3,4-THIADIAZOLYL-4 GROUPS

[75] Inventors: Graham Evans, Chelmsford, England; Mario Fryberg, Praroman-le-Mouret, Switzerland; Thomas Stauner, Marly, Switzerland; Paul Tschopp, Düdingen, Switzerland; David G. Leppard, Marly, Switzerland

[73] Assignee: Ciba-Geigy AG, Basel, Switzerland

[21] Appl. No.: 900,675

[22] Filed: Apr. 27, 1978

Related U.S. Application Data

[62] Division of Ser. No. 782,798, Mar. 20, 1977, Pat. No. 4,115,121.

[30] Foreign Application Priority Data

Apr. 14, 1976 [CH] Switzerland ............... 4751/76

[51] Int. Cl.$^2$ ............... C07D 285/12; C07D 401/12; C07D 401/14; C07D 409/04
[52] U.S. Cl. ............... 548/138; 260/239.95; 546/277; 548/139; 548/140
[58] Field of Search ............... 260/306.8 D, 294.8 D, 260/239.95; 546/277; 548/138, 139, 140

[56] References Cited

U.S. PATENT DOCUMENTS

| | | | |
|---|---|---|---|
| 2,312,040 | 2/1943 | Kendall et al. | 96/56.3 |
| 2,476,525 | 7/1949 | Anish et al. | 260/306.8 D |
| 2,672,417 | 3/1954 | Jennen | 96/100 |
| 3,245,788 | 4/1966 | Jaeken et al. | 96/56.3 |
| 3,874,948 | 4/1975 | Kertel | 96/56.5 |

*Primary Examiner*—Alton D. Rollins

[57] ABSTRACT

Color photographic material is provided which contains at least one silver halide emulsion layer containing a yellow color coupler of the formula

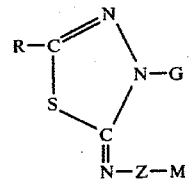

wherein G is the radical of a yellow coupler which is bonded to the heterocyclic ring by means of the active methylene group, Z is —CO— or —SO$_2$—, M is hydrogen if Z is —CO—, or a substituent and R is hydrogen or a substituent.

The new two-equivalent yellow couplers lead due to their improved reactivity (high maximum density), minimal fog and high fastness to light and outstanding spectral properties of the dyestuffs formed therefrom to a color photographic material of advantageous properties.

13 Claims, No Drawings

YELLOW PHOTOGRAPHIC COLOR COUPLERS CONTAINING 3-IMINO-1,3,4-THIADIAZOLYL-4 GROUPS

This is a division of application Ser. No. 782,798 filed Mar. 30, 1977, now U.S. Pat. No. 4,115,121.

In order to produce coloured photographic images, exposed silver halide emulsion layers which at the same time contain colour couplers are, as is known, developed with a developing agent which contains aromatic primary amino groups. The oxidised developing agent then reacts with the colour coupler with the formation of an image dyestuff, the amount of this dyestuff being dependent on the amount of incident light.

In general, a light-sensitive photographic multi-layer material which consists of a red-sensitive layer, which contains the cyan coupler, a green-sensitive layer, which contains the magenta coupler, and a blue-sensitive layer, which, in turn, contains the yellow coupler, is used. On colour development, the corresponding dyestuffs which are cyan, magenta and yellow in colour, are formed.

Usually, phenols or α-naphthols are employed as cyan couplers, pyrazolones are employed as magenta couplers and acylacetylamides are employed as yellow couplers. The dyestuffs formed after development are then indophenols, indamines or azomethines.

Conventional colour couplers possess an active methylene group and four equivalents of silver halide are required in order to convert these into the corresponding image dyestuff; therefore colour couplers of this type are called four-equivalent couplers. Colour couplers in which one hydrogen atom of the active methylene group is replaced by a group which can be split off during the coupling reaction are also known. In this case two equivalents of silver halide are required in order to produce the corresponding image dyestuff. Therefore, colour couplers of this type are termed two-equivalent couplers.

Compared with the four-equivalent couplers, two-equivalent couplers are distinguished by the advantages which follow:

1. The amount of silver halide required for the formation of the same amount of dyestuff is only half as great; there is thus a noticeable reduction in the manufacturing costs for a photographic material;
2. The light-sensitive layer can be kept thinner, by which means the sharpness and the resolution of the resulting colour image are improved; and
3. The sensitivity of the lower layers is increased as a result of the increased light transmittance, since the thickness of the upper layers is reduced.

In the case of the yellow couplers, essentially the following leaving groups have been proposed, to date, for two-equivalent couplers:

halogen atoms, such as are described, for example, in German Offenlegungsschrift No. 2,114,577, French Pat. Nos. 991,453 and 869,169 or U.S. Pat. Nos. 2,728,658 and 3,277,155;

the group —OR, in which R represents alkyl, aryl, a heterocyclic radical or acyl, such as are described, for example, in British Pat. No. 1,092,506, French Pat. Nos. 1,411,385 and 1,385,696 or in U.S. Pat. Nos. 3,447,928 and 3,408,194;

The —SR'' group which is described in British Pat. No. 953,454 or U.S. Pat. No. 3,265,506;

the 1,2,3-benztriazolyl group of the formula

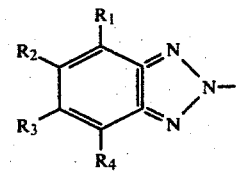

the radicals —SO$_3$H and —SCN (British Pat. No. 638,039 and U.S. Pat. No. 3,253,924)

imide groups of the formulae

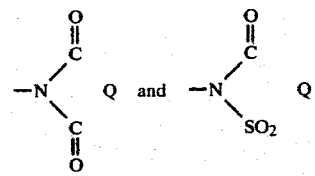

radicals of the formula

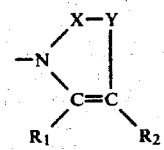

leaving groups of the formula

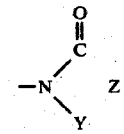

leaving groups of the formula

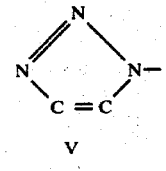

wherein V, together with —C═C— grouping, forms an aromatic ring of the benzene series or a heterocyclic ring with at least one nitrogen atom (German Offenlegungsschrift No. 2,414,006), leaving groups of the formula

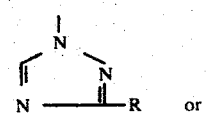

or

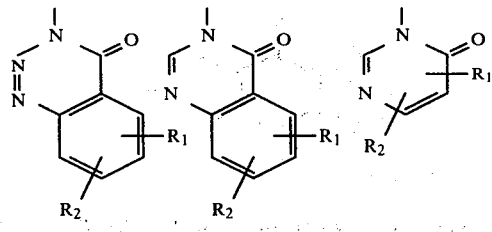

according to German Offenlegungsschrift No. 2,528,638 or in some cases according to German Offenlegungsschrift No. 2,442,703, leaving groups of the formula

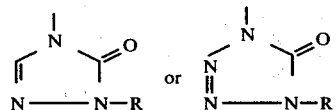

according to German Offenlegungsschrift No. 2,442,703 and certain pyridones and pyridazones according to German Offenlegungsschrift No. 2,318,807.

The object of the present invention is to provide readily accessible two-equivalent couplers, for materials for colour photography, which, compared with known two-equivalent couplers, are distinguished by improved reactivity (high maximum density), minimal fog, high fastness to light and outstanding spectral properties of the dyestuffs formed therefrom.

The subject of the invention is a material, for colour photography, which contains at least one silver halide emulsion layer which contains, as the yellow coupler, a compound of the formula

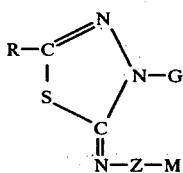

(1)

in which G is a radical of a yellow coupler, which is bonded to the heterocyclic ring by means of the active methylene group, Z is —CO— or —SO$_2$—, M is hydrogen, if Z is —CO—, or a substituent, for example alkyl with 1 to 18 carbon atoms, optionally substituted by halogen, hydroxyl, nitro, cyano, alkoxy, aryloxy or amino, aralkyl, cycloalkyl with 1 to 4 cycloalkyl rings, phenyl, optionally substituted by lower alkyl or lower alkoxy, halogen, acylamino, sulphonic acid groups, sulphonic acid amide groups, carboxylic acid groups, carboxyic acid amide groups, carboxylic acid ester groups, hydroxyl, nitro, cyano, amino, mercapto, alkylmercapto or —SO$_2$W or —COW, in which W is alkyl with 1 to 18 carbon atoms, optionally substituted by halogen, nitro, cyano, amino or alkoxy with 1 to 18 carbon atoms, cycloalkyl, aryl, pyridyl, pyrimidyl, furyl or thienyl, M is also pyridyl, furyl, thienyl or perfluoroalkyl, acyl or dialkylamino, with, in each case, up to 5 carbon atoms in the alkyl part, alkoxy with 1 to 18 carbon atoms or phenoxy and R is hydrogen or a substituent, such as, for example, alkyl with 1 to 18 carbon atoms, aralkyl, aryl, pyridyl, pyrimidyl, furyl, thienyl, cycloalkyl, alkoxy with 1 to 18 carbon atoms, aryloxy, alkylmercapto with 1 to 18 carbon atoms, arylmercapto, halogen, acyl, acyloxyalkyl, trifluoromethyl, cyano, a primary amino group, a mono- or di-alkylamino group, in which the alkyl radicals each contain 1 to 18 carbon atoms, or one of the groups M-Z-HN-, W-CO-, W—CON$\diagdown^E$—,

W-SO$_2$-, -SO$_2$NH$_2$,

—SO$_2$N$\diagup^E_{E'}$,

W—CO—O— or W—O—CO—, in which E is alkyl with 1 to 5 carbon atoms, E' is hydrogen or alkyl with 1 to 5 carbon atoms and M, W and Z have the indicated meanings.

The invention also relates to a process for the production of a yellow image, wherein a material, for colour photography, which contains, on a support, at least one silver halide emulsion layer containing, as the yellow coupler, at least one compound of the formula (1), is exposed and the exposed material is treated with an aqueous alkaline solution which contains an aromatic amine as the developer.

The invention also relates to the yellow images produced by this process.

The invention furthermore relates to the new yellow couplers of the formula (1).

The radicals G, of a yellow coupler, in compounds of the formula (1) are, as a rule, open-chain radicals, containing methylene groups, of yellow couplers, especially benzoylacetanilide or pivaloylacetanilide radicals, the latter being preferred.

The radical M in the compounds of the formula (1) can be hydrogen only when Z is —CO—. M is also alkyl with 1 to 18 carbon atoms and these alkyl radicals can be straight-chain or branched, such as, for example, methyl, ethyl, n-propyl, iso-propyl, n-butyl, iso-butyl, tert.-butyl, amyl, n-hexyl and n-heptyl; and octyl, nonyl, decyl, dodecyl, tridecyl, tetradecyl, pentadecyl, hexadecyl, heptadecyl, and octadecyl, including the various isomers in each case.

These alkyl radicals can be substituted by halogen atoms, especially fluorine, chlorine, (—CH$_2$Cl, —CCl$_3$) or bromine; hydroxyl, nitro or cyano; alkoxy, especially with 1 to 5 carbon atoms in the alkoxy part, such as, for example, —CH$_2$—O—C$_n$H$_{2n+1}$, in which n is 1 to 5; aryloxy, especially —CH$_2$O—⟨phenyl⟩ , —CH$_2$O—⟨phenyl⟩—t.amyl, —CH$_2$O—⟨phenyl(t.amyl)⟩—t.amyl , —CHO(n-C$_{12}$H$_{25}$)—⟨phenyl(t.amyl)⟩—t.amyl , —CHO(n-C$_{12}$H$_{25}$)—⟨phenyl⟩—t.amyl , [t.amyl : —C(CH$_3$)$_2$(C$_2$H$_5$)].

amino, such as, for example, $-NH_2$, $-NHC_nH_{2n+1}$ or $-N(C_nH_{2n+1})_2$, in which n is 1 to 5. M is also cycloalkyl, such as cycloalkyl with 1 to 4 cycloalkyl rings and 5 to 10 carbon atoms, for example pentyl, hexyl, norbornyl or 1-adamantyl; aralkyl, especially benzyl; phenyl, optionally substituted by $-C_nH_{2n+1}$ or $-O-C_nH_{2n+1}$, in which n is 1 to 5, for example, methyl, ethyl, propyl, butyl, amyl and isomeric radicals or methoxy, ethoxy, propoxy, butoxy, pentoxy and isomeric radicals, halogen, especially chlorine and bromine, or acylamino, especially $-NHCOC_nH_{2n+1}$ and

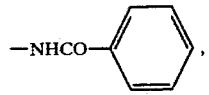

in which n is 1 to 5; $SO_3H$, sulphonic acid amide groups, such as $-SO_2NH_2$, $-SO_2N(C_nH_{2n+1})_2$ and $-SO_2NH(C_nH_{2n+1})$, $-COOH$, carboxylic acid amide groups, such as $-CONH_2$, $-CON(C_nH_{2n+1})_2$ and $-CONH(C_nH_{2n+1})$, carboxylic acid ester groups, such as $-COOC_nH_{2n+1}$,

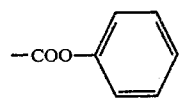 and 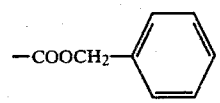

hydroxyl, nitro, cyano, amino groups, such as $-NH_2$, $-NHC_nH_{2n+1}$ or $-N(C_nH_{2n+1})_2$, mercapto ($-SH$) or alkylmercapto, especially of the formula $-SC_nH_{2n+1}$. Further substituents on the phenyl nucleus can correspond to the formula $-SO_2W$ or $-COW$, in which W can be alkyl with 1 to 18 carbon atoms (as indicated above). The alkyl radicals W can be substituted by halogen, for example chlorine or bromine, nitro, cyano, amino or alkoxy with 1 to 18 carbon atoms. Cycloalkyl, especially cyclohexyl, aryl, especially phenyl, which is optionally also substituted, pyridyl, pyrimidyl, furyl or thienyl are further meanings of W. The radical M can also be pyridyl, furyl or thienyl, perfluoroalkyl, especially a radical of the formula $C_nF_{2n+1}$, acyl, such as, for example, benzoyl, dialkylamino, especially of the formula $-N(C_nH_{2n+1})_2$, alkoxy with 1 to 18 carbon atoms ($-OC_mH_{2m+1}$, m=1 to 18) or phenoxy

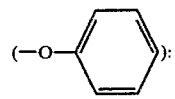

the index n always has the meaning 1 to 5.

The radical R in the compounds of the formula (1) is hydrogen, alkyl with 1 to 18 carbon atoms (as indicated above), aralkyl, especially benzyl, or aryl, especially phenyl and also phenyl substituted by halogen (Cl or Br), $-CN$, $-NO_2$, $-OH$, $-O-C_mH_{2m+1}$, $-C_mH_{2m+1}$, $-NH_2$,

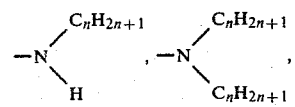

$-NH-OC-W_1$, $-NH-SO_2-W_1$, $-CO-W_1$, $-SO_2-W_1$, $-S-C_mH_{2m+1}$, sulphonic acid amide (including those having substituents on the nitrogen atom), carboxylic acid amide (including those having substituents on the nitrogen atom), $-COOH$ or $-COOW_1$.

$W_1$ can have the following meanings: $-C_mH_{2m+1}$ (m=1 to 18), cyclohexyl, adamantyl, phenyl which is optionally further substituted by $-C_mH_{2m+1}$, $-O-C_mH_{2m+1}$, $-Cl$, $-Br$, $-CN$, $-OH$, $-NH-OC-C_nH_{2n+1}$,

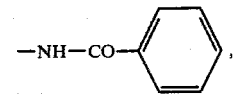

$-S-C_mH_{2m+1}$, $-SO_2-C_nH_{2n+1}$,

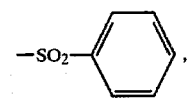

sulphonic acid amide (including those having substituents on the nitrogen atom), carboxylic acid amide (including those having substituents on the nitrogen atom), $-COOH$, $-CO-O-C_nH_{2n+1}$,

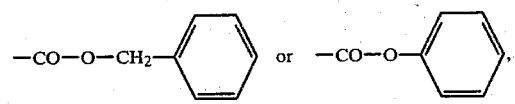

pyridyl, furyl or thienyl.

The radical R is also pyridyl, pyrimidyl, furyl, thienyl, cycloalkyl, especially with 1 to 4 cycloalkyl rings and 6 to 10 carbon atoms, such as, for example, cyclohexyl, norbornyl or 1-adamantyl, alkoxy with 1 to 18 carbon atoms (alkoxy radicals analogous to the alkyl radicals mentioned), alkoxy with 1 to 5 carbon atoms, such as methoxy, ethoxy, n- and iso-propoxy, n-butoxy and n-pentoxy, being preferred, or aryloxy, especially phenoxy, alkylmercapto with 1 to 18, and especially 1 to 8, carbon atoms, such as, for example, methylmercapto, ethylmercapto, n-propylmercapto, iso-propylmercapto, butylmercapto, pentylmercapto, hexylmercapto, heptylmercapto and octylmercapto, arylmercapto, especially phenylmercapto, halogen, especially chlorine and bromine, acyl, especially benzoyl, acyloxyalkyl, especially benzoyloxyalkyl with 1 to 5 carbon atoms in the alkyl part, for example

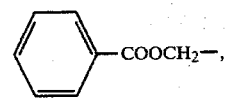

trifluoromethyl, cyano, an amino group, especially $-NH_2$ or

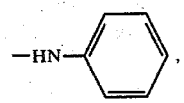

or a mono- or di-alkylamino group with 1 to 18 carbon atoms in the alkyl part, especially of the formulae $-NHC_nH_{2n+1}$ and $N(C_nH_{2n+1})$, in which n is 1 to 5; in addition, R can also denote the radicals M—Z—NH—, W—CO—, especially $W_1CO$—,

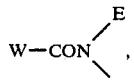

especially

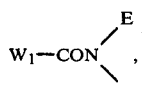

$W-SO_2-$, especially $W_1SO_2$, $-SO_2NH_2$,

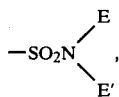

W—COO—, especially $W_1$—COO—, and WOCO—, especially $W_1OCO$—. M, W, $W_1$ and Z have the indicated meanings, E is alkyl with 1 to 5 carbon atoms and E' is hydrogen or alkyl with 1 to 5 carbon atoms.

The data regarding further substitution are to be understood to mean that the particular radicals can contain one or more than one of the indicated substituents. The dialkylamino groups of the formula

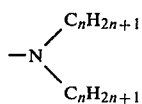

can also contain two different alkyl groups on the same nitrogen atom.

The substituent G in the compounds of the formula (1) is a radical, especially an open-chain radical, of a yellow coupler which is bonded by means of the active methylene group, that is to say the carbon atom bonded to the thiadiazolyl ring is not a constituent of a ring. Preferably, the substituent G is an acylacetic acid amide radical which is bonded to the thiadiazolyl ring by means of the α-carbon atom of the acetic acid group, acyl (Q—CO—) being, in particular, pivaloyl and optionally substituted benzoyl and amide being, in particular, anilide which is optionally substituted on the phenyl ring.

Further possible acyl radicals (Q—CO—) are those in which Q is alkyl with at most 32 carbon atoms, α-alkoxyalkyl with 2 to 32 carbon atoms, α-aryloxyalkyl with 7 to 40 carbon atoms, cycloalkyl with 1 to 4 alicyclic rings, or an aryl (preferably benzene) or heterocyclic radical which is optionally further substituted by alkyl or alkoxy with 1 to 18 carbon atoms, halogen, such as chlorine or bromine, acylamino (especially derived from carboxylic acids), sulphonic acid amide or carboxylic acid amide.

The aryl or heterocyclic radical can be substituted by one or more substituents.

Preferred radicals Q are tertiary butyl, norbornyl, [2,2,2]-bicyclooctyl, phenyl, 3,4-methylenedioxyphenyl or p-methoxyphenyl.

The phenyl ring of the anilide can be substituted by one or more of the following substituents: halogen, such as chlorine or bromine, alkyl and alkoxy, especially with 1 to 5 carbon atoms, acylamino, preferably derived from carboxylic acids, sulphonic acid amide, carboxylic acid amide or carboxylic acid esters, especially carboxylic acid alkyl esters.

The acylamino or carbox(sulphon)amido groups can also carry the ballast groups which are customary for colour couplers and are in themselves known.

The materials, according to the invention, for colour photography contain, as yellow couplers, in particular compounds of the formula (1), in which G is a radical of a yellow coupler which is bonded to the heterocyclic ring by means of the active methylene group, Z is —CO— or —SO₂—, M is hydrogen, if Z is —CO—, or alkyl with 1 to 18 carbon atoms, optionally substituted by halogen, nitro, cyano, alkoxy or amino, aralkyl, cycloalkyl, phenyl, optionally substituted by alkyl, alkoxy, halogen, acylamino, sulphonic acid groups, sulphonic acid amide groups, carboxylic acid groups, carboxylic acid amide groups, carboxylic acid ester groups, hydroxyl, nitro, cyano, amino, mercapto, alkylmercapto or —SO₂—W or —CO—W, in which W is alkyl with 1 to 18 carbon atoms, optionally substituted by halogen, nitro, amino or alkoxy with 1 to 18 carbon atoms; or W is cycloalkyl, aryl, pyridyl, pyrimidyl, furyl or thienyl; M is also pyridyl, furyl, thienyl or perfluoroalkyl, acyl or dialkylamino, with, in each case, 5 carbon atoms in the alkyl part, alkoxy with 1 to 18 carbon atoms or phenoxy and R is hydrogen, alkyl with 1 to 18 carbon atoms, aralkyl, aryl, cycloalkyl, alkoxy with 1 to 18 carbon atoms, aryloxy, alkylmercapto with 1 to 18 carbon atoms, arylmercapto, halogen, trifluoromethyl, cyano, a primary amino group or a mono- or dialkylamino group, the alkyl radicals of which each contain 1 to 18 carbon atoms, or one of the groups

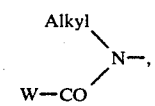

in which alkyl contains 1 to 5 carbon atoms, M—Z—HN—, W—CO—, W—SO₂—, W—CO—O— and W—O—CO—, in which M, W and Z have the indicated meanings.

In some cases compounds of the formula

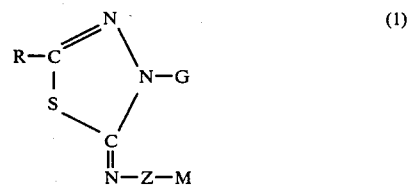

(1)

in which G, Z, M and R have the indicated meaning but at least one of the radicals M and R contains a benzene nucleus and these benzene nuclei are preferably bonded direct to the heterocyclic radical or to Z, prove to be valuable yellow couplers.

Materials, for colour photography, which contain, as yellow couplers, compounds of the formula

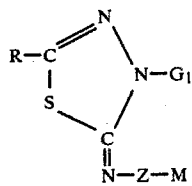 (2)

in which G₁ is an open-chain radical, containing a methylene group, of a yellow coupler and R, M and Z have the indicated meanings, or of the formula

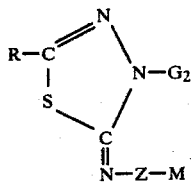 (3)

in which G₂ is a benzoylacetanilide or pivaloylacetanilide radical and R, M and Z have the indicated meanings, are also particularly suitable.

Preferred representatives of the compounds of the formula (3) are those of the formulae

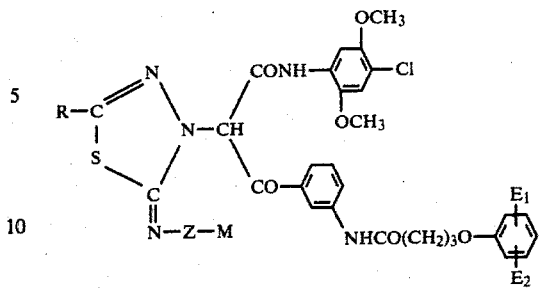 (4)

in which $E_1$ is alkyl with 1 to 20 carbon atoms and $E_2$ is hydrogen or alkyl with 1 to 20 carbon atoms and R, M and Z have the indicated meanings, and

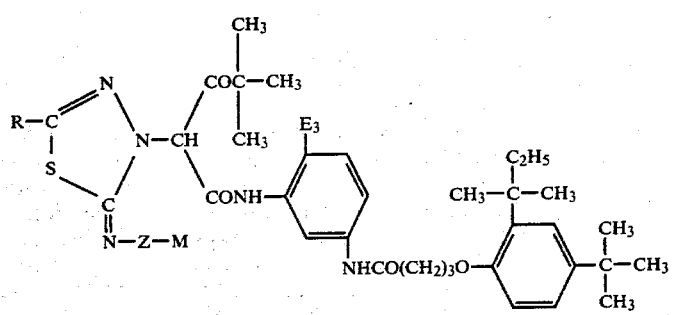 (5)

in which $E_3$ is chlorine and alkyl or alkoxy with 1 to 4 carbon atoms and R, M and Z have the indicated meanings. $E_3$ in formula (5) is preferably chlorine.

Materials, for colour photography, which contain, as yellow couplers, compounds of the formulae

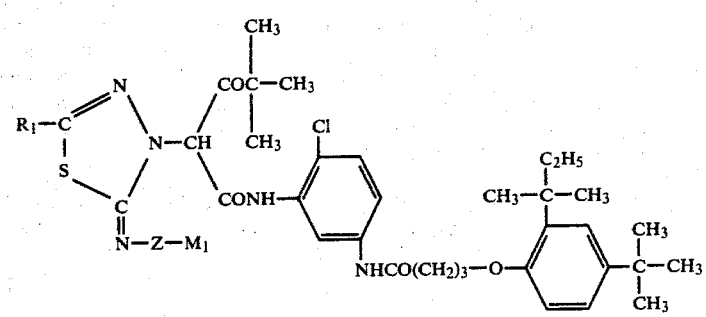 (6)

in which $M_1$ is alkyl with 1 to 13 carbon atoms, optionally substituted by halogen, alkoxy with 1 to 5 carbon atoms or optionally substituted phenoxy; alkoxy with 1 to 5 carbon atoms; benzyl, cycloalkyl, phenyl, optionally substituted by alkyl or alkoxy with 1 to 5 carbon atoms, halogen, nitro or —NHCOC$_n$H$_{2n+1}$, in which n is 1 to 5; pyridyl, phenylamino or dialkylamino with in each case, 1 to 5 carbon atoms in the alkyl part, $R_1$ is hydrogen, alkyl with 1 to 12 carbon atoms, benzyl, phenyl, thienyl, cycloalkyl with 1 to 4 cycloalkyl rings, alkoxy with 1 to 5 carbon atoms, alkylmercapto with 1 to 4 carbon atoms, halogen, benzoyl, benzoyloxyalkyl with 1 to 5 carbon atoms in the alkyl part, benzylamino, mono- or di-alkylamino with 1 to 5 carbon atoms in the alkyl part, SO₂NH₂, N,N-dialkylsulphonamide with, in each case, 1 to 5 carbon atoms in the alkyl part, or —NHCOC$_n$H$_{2n+1}$, in which n is 1 to 5, and Z is —CO— or —SO₂—, and

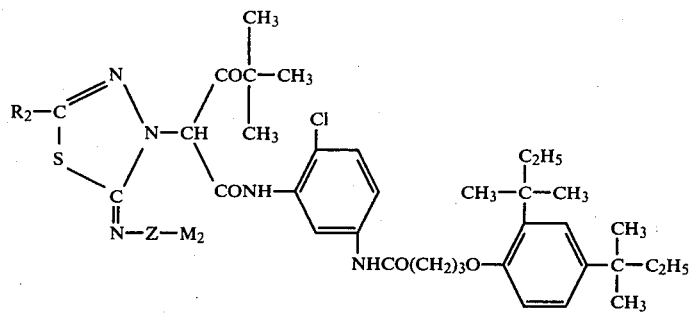

(7)

in which $M_2$ is straight-chain or branched alkyl with 1 to 7 carbon atons, —$CH_2Cl$, —$CCl_3$, —$CH_2OC_2H_5$,

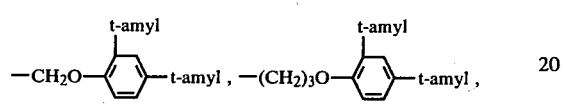

alkoxy with 1 or 2 carbon atoms, benzyl, phenyl, tolyl, t-butylphenyl, methoxyphenyl, dimethoxyphenyl, chlorophenyl, dichlorophenyl, nitrophenyl, acetylaminophenyl, pyridyl, anilino or dimethylamino, $R_2$ is hydrogen, alkyl with 1 to 12 carbon atoms, phenyl, benzyl, thienyl, cyclohexyl, norbornyl, 1-adamantyl, alkoxy with 1 to 3 carbon atoms, alkylmercapto with 1 to 4 carbon atoms, chlorine, bromine, benzoyl, benzoyloxyalkyl with 1 to 3 carbon atoms in the alkyl part, benzylamino, mono- or dialkylamino with 1 or 2 carbon atoms in the alkyl part, N,N-dialkylsulphonamide with 1 or 2 carbon atoms in the alkyl part or —NH-$COC_{n_1}H_{2n_1+1}$, in which $n_1$ is 1 or 2, and Z is —CO— or —$SO_2$—, are also particularly preferred.

The radical $R_2$ in the compounds of the formula (7), in which Z is, in particular, —CO—, is preferably hydrogen, alkyl with 1 to 12 carbon atoms, phenyl, benzyl, thienyl, cyclohexyl, 1-adamantyl, methoxy, ethoxy, propoxy, methylmercapto, propylmercapto, chlorine, bromine, benzoyl, benzoyloxymethyl, benzylamino, methylamino, diethylamino, —$SO_2N(CH_3)_2$ or —NH-$COCH_3$.

Finally, materials, for colour photography, which contain, as yellow couplers, compounds of the formula

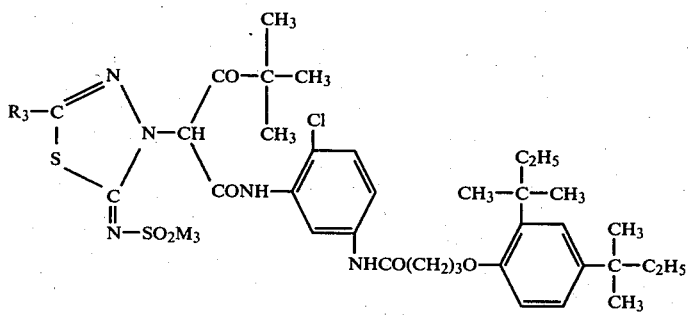

in which $M_3$ is methyl, t-butyl, p-tolyl, p-chlorophenyl or p-acetylaminophenyl and $R_3$ is hydrogen, alkyl with 1 to 10 carbon atoms, cyclohexyl, 1-adamantyl, methoxy, i-propoxy, methylmercapto, chlorine, bromine, phenyl, benzyl or thienyl, are also particularly valuable.

The leaving groups of the formula

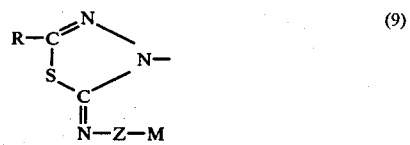

(9)

in which M, R and Z have the indicated meanings, can be introduced into the yellow couplers using known starting materials.

Appropriately, 2-acylamino-1,3,4-thiadiazoles are reacted, in a manner which is in itself known, with halogen compounds of the formulae Cl-G or Br-G (in which the halogen atom replaces a hydrogen atom of the active methylene group of the corresponding four-equivalent coupler) in inert organic solvents, such as acetonitrile, propionitrile or dimethylformamide, in the presence of an acid-binding agent, to give the compounds, according to the invention, of the formulae (1) to (8). The azeniate ion corresponding to the 2-acylamino-1,3,4-thiadiazole can also be synthesised independently and then reacted with the compounds Cl-G or Br-G. This azeniate ion, which primarily is also formed from the 2-acylamino-1,3,4-thiadiazole and the acid-binding agent, has the following formula, to which a corresponding mesomeric canonical formula can be assigned.

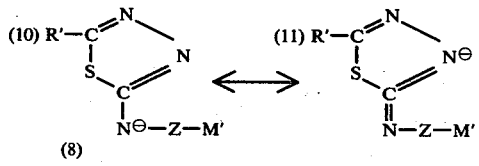

Depending on the relative electron density on the two nitrogen atoms participating in the mesomerism, which density in turn, of course, depends on the substituents R and —Z—M, the reaction with the reactant G-Cl or G-Br can now take place either on the ring nitrogen or on the exocyclic nitrogen. As a result, the corresponding isomeric compounds are then formed. This behaviour has been described in the literature for other mesomeric educts and in the case of ambident anions (in this connection compare, for example, R. Gompper, Angew. Chem. 76, 412 [1964]).

It has also been found that, in the category of compounds investigated, this isomerism (when it occurs at all) has no influence on the use properties which are sought. Therefore, a detailed description of the isomeric forms possible in each case is dispensed with. However, it is obvious that each of the possible forms can be used for the desired application.

The yellow couplers according to the invention represent a category of compounds which, in itself, is new. They are distinguished by high reactivity (high maximum density), minimal fogging, high fastness to light, both of the couplers and of the dyestuffs formed, and excellent spectral properties of the dyestuffs formed.

According to the reaction equation

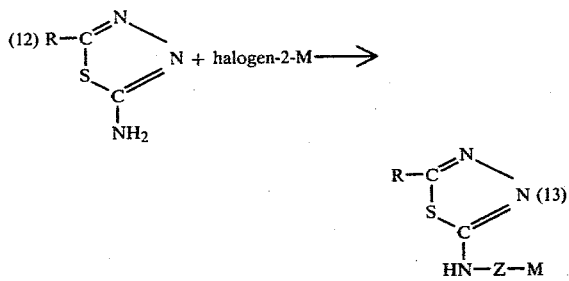

the compounds of the formula (13) can be manufactured from the 2-amino-1,3,4-thiadiazoles of the formula (12) by known methods by reacting the aminothiadiazole of the formula (12) in the presence of bases, in an inert organic solvent, with an acid chloride or acid bromide, as is described, for example, in J. Indian Chem. Soc. Vol. LII, May 1975, page 433–435 and in J. Chem. Soc. (C), 2700 (1967). The acid halides, in which Z denotes a —CO— group, are derived, for example, from the following carboxylic acids and carboxylic acid derivatives: acetic acid, formic acid, propionic acid, butyric acid, isobutyric acid, 2-methylbutyric acid, valeric acid, isovaleric acid, caproic acid, caprylic acid, capric acid, dodecanoic acid, tetradecanoic acid, palmitic acid, stearic acid, cyclohexanecarboxylic acid, pivalic acid, chloroacetic acid, dichloroacetic acid, trichloroacetic acid, methoxyacetic acid, ethoxyacetic acid, phenylacetic acid, phenoxyacetic acid, 2,4-di-t-pentylphenoxyacetic acid, 4-t-pentylphenoxyacetic acid, N,N-dimethylcarbamic acid, monomethyl carbonate, monomethoxyethyl carbonate, monoisopropyl carbonate, monoisobutyl carbonate, monophenyl carbonate, monobenzyl carbonate, mono-t-butyl carbonate, benzoic acid, o-toluic acid, m-toluic acid p-toluic acid, o-chlorobenzoic acid, m-chlorobenzoic acid, p-chlorobenzoic acid, m-methoxybenzoic acid, p-methoxybenzoic acid, p-bromobenzoic acid, m-dimethylaminobenzoic acid, m-cyanobenzoic acid, p-cyanobenzoic acid, p-methylsulphonylbenzoic acid, m-methylsulphonylbenzoic acid, m-trifluoromethylbenzoic acid, 3,4-dimethylbenzoic acid, 2,4-dimethylbenzoic acid, 3,4-dimethoxybenzoic acid, 3,5-dimethoxybenzoic acid, 2,4-dimethoxybenzoic acid, p-t-butylbenzoic acid, 3,4-dichlorobenzoic acid, 2,4-dichlorobenzoic acid, pyridine-2-carboxylic acid, pyridine-3-carboxylic acid, pyridine-4-carboxylic acid, thiophene-2-carboxylic acid, furane-2-carboxylic acid, naphthalene-1-carboxylic acid, naphthalene-2-carboxylic acid, 4-methoxycarbonylbenzoic acid and 4-ethoxycarbonylbenzoic acid.

The sulphonic acid halides, in which Z denotes a $—SO_2—$ group, are derived, for example, from the following sulphonic acids: methanesulphonic acid, trifluoromethanesulphonic acid, benzenesulphonic acid, p-acetylaminobenzenesulphonic acid, o- or p-toluenesulphonic acid, xylenesulphonic acid, pyridine-3-sulphonic acid, naphthalene-1-sulphonic acid and naphthalene-2-sulphonic acid.

The aminothiadiazoles of the formula (12) are compounds which are known from the literature. They can be manufactured by various methods, such as, for example, are described in J. Indian Chem. Soc. Vol. LII, May 1975, page 433-35, in U.S. Pat. No. 2,623,877, in J. Chem. Soc. (C), 2702 [1967], in Acta Chimica Scandinavica 18, 174–184 [1964], in J. Het. Chem. Vol. 12, 581, 841 [1975], in J. Chem. Soc. (C) 2932 [1971], in J. Chem. Soc. (C) 2927 [1971], in Eur. J. Med. Chem. 10, page 121–24 [1975], J. Chem. Soc. 1163 [1949], in British Pat. No. 916,061, J. Prakt. Chemie 122, 289 [1929], J. Prakt. Chemie 122, 303 [1929] and J. Chem. Soc. 1509 [1958]. The following atoms or groupings can be mentioned as radicals R in formula (12): hydrogen, methyl, ethyl, propyl, isopropyl, butyl, isobutyl, t-butyl, hexyl, cyclohexyl, heptyl, undecyl, ethoxymethyl, hydroxymethyl, benzyl, methoxy, hydroxyl, ethoxy, isopropoxy, propoxy, butoxy, phenoxy, acetoxy, benzoyloxy, amino, acetylamino, methylamino, dimethylamino, phenylamino, chlorine, bromine, methylmercapto, ethylmercapto, propylmercapto, isopropylmercapto, phenylmercapto, methylsulphonyl, phenylsulphonyl, acetyl, benzoyl, methylsulphonylamino, phenyl, 4-methoxyphenyl, 3,5-dimethoxyphenyl, 2-methoxyphenyl, 3-methoxyphenyl, 2-chlorophenyl, 3,4-dichlorophenyl, 4-chlorophenyl, 4-cyanophenyl, 4-nitrophenyl, 2-methylphenyl, 4-methylphenyl, 3-methylphenyl, 4-methylsulphonylphenyl, 4-bromophenyl, 3-dimethylaminophenyl, 1-naphthyl, 2-naphthyl, 2-pyridyl, 3-pyridyl, 4-pyridyl and 2-thienyl.

Starting materials of the formulae Cl-G and Br-G which can be employed for the synthesis of the yellow coupler according to the invention are the α-halogenoacylacetanilides, which are known to those skilled in the art, such as the α-halogenoacylacetanilides which are described, inter alia, in German Offenlegungsschrift No. 2,114,577, French Pat. Nos. 991,453 and 869,169 and U.S. Pat. Nos. 2,728,658 and 3,277,155.

Thus, for example, the following compounds can be used:

1. α-Acetyl-α,2-dichloro-5-[α-(2′,4′-di-tert.-amylphenoxy)-acetylamino]-acetanilide.
2. α-Pivalyl-α-bromo-2-chloro-5-[α′-(4′-tert.-amylphenoxy)-n-tetradecanoylamino]-acetanilide.
3. α(β′-Methoxy-α,α′-dimethyl-propionyl)-α-chloro-4-[N-(γ″-phenylpropyl)-N-(p-tolyl)-carbamoylmethoxy]-acetanilide.
4. α-(α′-Methoxyisobutyryl)-α-chloro-2-methoxy-5-[γ-(3″-n-pentadecylphenoxy)-butyramino]-acetanilide.
5. α-(α′-Phenoxyisobutyryl)-α,2-dichloro-5-(n-octadecyl-succinimido)-acetanilide.
   thylbutyryl)-α-chloro-acetylamino]-2-phenoxybenzene-5-carboxylic acid (di-n-butoxy)-phosphonoe-
6. 1-[α-(α′,α′-Dimethylbutyryl)-α-chloro-acetylamino]-2-phenoxybenzene-5-carboxylic acid (di-n-butoxy)- phosphonoethylamide [—CO—NH—CH$_2$—CH$_2$—(OP)-(O—C$_4$H$_9$)$_2$].
7. α-(α',α'-Dimethyl-octadecanoyl)-α-bromo-3,5-bis-methoxycarbonyl-acetanilide.
8. α-(α'-Ethyl-α'-methyl-hexanoyl)-α-bromo-2-chloro-5-[γ''-(2'',4''-di-tert.-amylphenoxy)-butyramino]-acetanilide.
9. α-(α', α', γ', γ'-tetramethyl-valeryl)-α,2-dichloro-5-(n-dodecyloxycarbonyl)-acetanilide.
10. α-(1'-Methyl-cyclohexanecarbonyl)-α-bromo-2-chloro-5-[α''-(2'',4''-di-tert.-amylphenoxy)-butyramino]-acetanilide.
11. α-(7',7'-Dimethylnorbornane-1'-carbonyl)-α,2-dichloro-5-[α''-(2'',4''-di-tert.-amylphenoxy)-acetamino]-acetanilide.
12. α-Benzoyl-α-chloro-2-methoxy-5-[α'-(3'-n-dodecyloxyphenoxy)-butyramino]-acetanilide.
13. 1-[α-(4'-Methoxybenzoyl)-α-chloro]-acetylamino-2-chloro-5-[β-(N-palmityl-N-n-butyl-amino)-propionylamino]-benzene.
14. α-Piperonyloyl-α,2-dichloro-5-(α'-phenoxy-n-tetradecanoylamino)-acetanilide.
15. (α'-n-Dodecyloxycarbonyl)-ethyl 1-[α-(2'-chlorobenzoyl)-α-chloro]-acetylaminobenzene-4-carboxylate.
16. α-(4'-Chlorobenzoyl)-α-bromo-2-hexadecyloxy-acetanilide.
17. α-Piperonyloyl-α-chloro-3-[(N-methyl-N-n-octadecyl)-sulphamoyl]-acetanilide.
18. α-{3'-[γ-(2'',4''-Di-t-amylphenoxy)-butyramino]-benzoyl}-α-bromo-4-chloro-2,5-dimethoxy-acetanilide.
19. α-{3'-[α''-(3''-n-Pentadecylphenoxy)-butyramino]-benzoyl}-α,2-dichloro-acetanilide, and
20. α-(4'-n-Hexadecyloxy-benzoyl)-α-chloro-2-methoxy-acetanilide.

The colour couplers of the formulae (1) to (8) can be incorporated, in a known manner, in photographic layers, for example silver halide emulsions containing gelatine or binders.

For example, they can be used with silver bromide, silver chloride or silver iodide emulsions or with those emulsions which contain a mixture of silver halides, such as silver bromide/iodide or silver chloride/bromide emulsions.

The emulsions can be chemically sensitised and they can also contain customary organic stabilisers and anti-fogging agents as well as customary plasticisers, such as, for example, glycerol. The emulsions can also be hardened using the hardeners customary for gelatine. Furthermore, the emulsions can contain customary coating auxiliaries. The emulsions can be applied to customary layer carriers for photographic recording material. A mixture of several colloids can optionally be used for dispersing the silver halides.

The customary developer baths can be employed for developing the recording material for colour photography. These baths as a rule contain a developing agent of the p-phenylenediamine type, a development retarder, such as potassium bromide, an antioxidant, such as sodium sulphite, and a base, for example, an alkali metal hydroxide or alkali metal carbonate. The developer baths can also contain a customary anti-fogging agent and complex-forming agents.

Corresponding application possibilities are described, for example, in U.S. Pat. Nos. 2,304,939, 2,304,940, 2,322,027, 2,284,879, 2,801,170, 2,801,171, 2,749,360 and 2,825,382.

General instructions for the manufacture of compounds of the formula (13) (leaving groups)

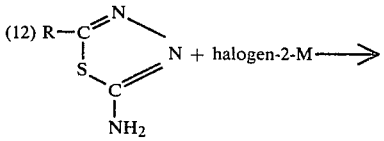

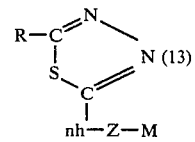

1 mol of the aminothiadiazole (12) is suspended in 500 ml of pyridine and the suspension is cooled to 0° to 10°. 1 mol of the carboxylic acid chloride (or of the corresponding sulphonic acid chloride) is added, with continuous stirring and cooling. The solution is allowed to react for 1 hour at 0° to 10° C. and is then further stirred for between 2 and 6 hours at room temperature. After concentrating to half its volume, the reaction mixture is poured into 1 l of water which previously has been acidified (pH value: 2) with 2 N sulphuric acid. A precipitate separates out and this is filtered off, washed with water until neutral, dried and recrystallised from ethanol.

If the corresponding isocyanate is used in place of the acid chloride, a compound of the formula (13) in which —Z—M is —CO—NHR is formed in an analogous manner.

Examples of compounds of the formula (13) are given in Table I which follows.

TABLE 1

| No. | R | —Z— | M | Melting point °C. |
|---|---|---|---|---|
| 101 | ⌬— | —CO— | —⌬ | 223–225 |
| 102 | CH$_3$O— | —CO— | —⌬ | 211–213 |
| 103 | CH$_3$O— | —SO$_2$— | —⌬—CH$_3$ | 166–167 |
| 104 | H— | —CO— | —CH$_3$ | 277–279 |

TABLE 1-continued
| No. | R | -Z- | M | Melting point °C. |
|-----|---|-----|---|-------------------|
| 105 | CH₃— | —CO— | —CH₃ | >280 |
| 106 | H— | —CO— | —C₂H₅ | 234–235 |
| 107 | CH₃— | —CO— | —CH₂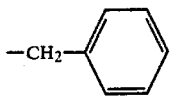 | 243–244 |
| 108 | CH₃— | —CO— | 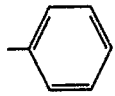 | 238–239 |
| 109 | CH₃— | —CO— | —(CH₂)₁₂CH₃ | 196–199 |
| 110 | CH₃— | —CO— | 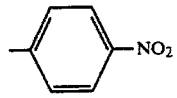 | >270 |
| 111 | CH₃— | —CO— | 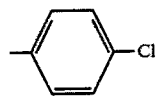 | 242–244 |
| 112 | CH₃—S— | —CO— | —CH₃ | 203–204 |
| 113 | 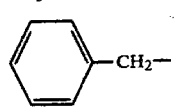—CH₂— | —CO— | —CH₃ | 243–245 |
| 114 | CH₃— | —CO— | 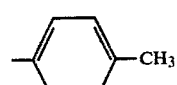 | 248–249 |
| 115 | CH₃— | —CO— | —CCl₃ | 207–209 |
| 116 | 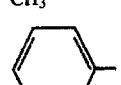 | —CO— | 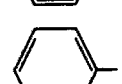 | 263–264 |
| 117 | 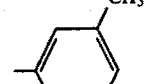 | —CO— |  | 201–203 |
| 118 | 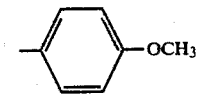 | —CO— |  | 160–162 |
| 119 | 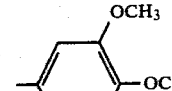 | —CO— |  | 272–273 |
| 120 | 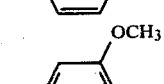 | —CO— |  | 212–213 |
| 121 | 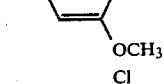 | —CO— | 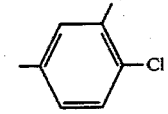 | 280–281 |
| 122 | Cl— | —CO— |  | 222–225 |

TABLE 1-continued
| No. | R | —Z— | M | Melting point °C. |
|---|---|---|---|---|
| 123 | 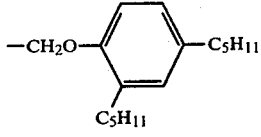 | —CO— | —C(CH$_3$)$_3$ | 193–195 |
| 124 | 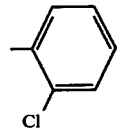 | —CO— | 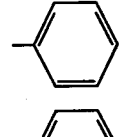 | 196–198 |
| 125 | 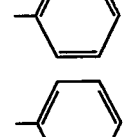 | —CO— | —CH$_2$Cl | 222–223 |
| 126 | 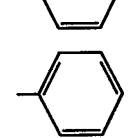 | —CO— | 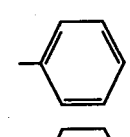 | 208–209 |
| 127 | CH$_3$S— | —CO— | 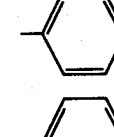 | 199–201 |
| 128 | 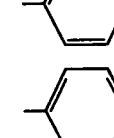 | —CO— | 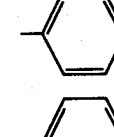 | 225–230 |
| 129 | H$_3$C—(H$_2$C)$_3$— | —CO— | 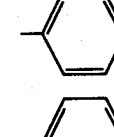 | 151–156 |
| 130 | H$_3$C—(H$_2$C)$_6$— | —CO— | 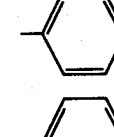 | 108–113 |
| 131 | (H$_3$C)$_2$—HC— | —CO— | 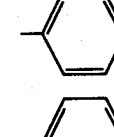 | 154–158 |
| 132 | H$_3$C—(H$_2$C)$_{10}$— | —CO— | 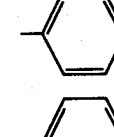 | 124–127 |
| 133 | 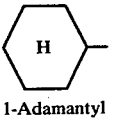 | —CO— | 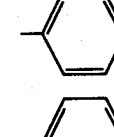 | 170–174 |
| 134 | 1-Adamantyl | —CO— | 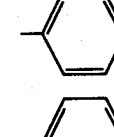 | 296–300 |
| 135 | (H$_3$C)$_3$C— | —CO— | 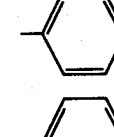 | 224–230 |
| 136 | 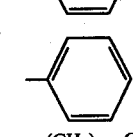 | —CO— | —(CH$_2$)$_6$—CH$_3$ | 132–135 |
| 137 | H$_3$C—(H$_2$C)$_6$— | —CO— | —C(CH$_3$)$_3$ | 56–59 |
| 138 | (H$_3$C)$_3$C— | —CO— | —C(CH$_3$)$_3$ | 183–186,5 |
| 139 | H$_3$C—(H$_2$C)$_{10}$— | —CO— | —C(CH$_3$)$_3$ | 64–68 |

TABLE 1-continued
| No. | R | —Z— | M | Melting point °C. |
|---|---|---|---|---|
| 140 | 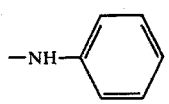 C₆H₅—CH₂— | —CO— | —C(CH₃)₃ | 157–160 |
| 141 | H₃C—(H₂C)₃— | —CO— | —C(CH₃)₃ | 100–105 |
| 142 | C₆H₅— | —CO— | —(CH₂)₃CH₃ | 199–200 |
| 143 | H₃C—(H₂C)₃— | —CO— | —(CH₂)₃CH₃ | 153–156 |
| 144 | H₃C—(H₂C)₃— | —CO— | —CCl₃ | wax-like |
| 145 | (H₃C)₂—HC—H₂C— | —CO— | —CCl₃ | wax-like |
| 146 | C₆H₅—CH₂— | —CO— | —N(CH₃)₂ | 133–141 |
| 147 | H₃C—(H₂C)₃— | —CO— | —NH—C₆H₅ | 199–200 |
| 148 | (H₃C)₂—HC— | —CO— | 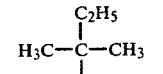 | 143–150 |
| 149 | (H₃C)₃C— | —CO— | 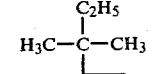 | 104–116 |
| 150 | C₆H₅— | —CO— | 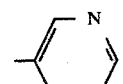 3-pyridyl | 233–236 |
| 151 | 2-thienyl 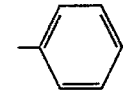 | —CO— | —C(CH₃)₃ | 184–186 |
| 152 | C₆H₅— | —CO— | —O—CH₂—CH₃ | 188–190 |
| 153 | (CH₃)₂CH—S— | —CO— | —O—CH₂—CH₃ | 117–119 |
| 154 | CH₃—S— | —CO— | —O—CH₂—CH₃ | 160–161 |
| 155 | (CH₃)₂CH—S— | —CO— | —C(CH₃)₃ | 103–105 |
| 156 | CH₃—CH₂—S— | —CO— | C₆H₅— | 129–132 |
| 157 | (CH₃)₂CH—S— | —CO— | 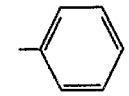 biphenyl | 145–147 |

TABLE 1-continued

| No. | R | —Z— | M | Melting point °C. |
|---|---|---|---|---|
| 158 | (CH₃)₂N—SO₂— | —CO— | —CH₃ | 253–255 |
| 159 | (CH₃)₂CH—O— | —CO— | phenyl | 187–189 |
| 160 | CH₃O— | —CO— | —C(CH₃)₃ | 163–165 |
| 161 | CH₃S— | —CO— | —C(CH₃)₃ | 161–163 |
| 162 | CH₃S— | —CO— | —CH₂OCH₂CH₃ | 117–118 |
| 163 | phenyl | —CO— | 2,4-dichlorophenyl | >250 |
| 164 | C₆H₅—CO— | —CO— | phenyl | 236–240 |
| 165 | (CH₃)₂CH—CH₂— | —CO— | —OCH₃ | 225–227 decomposition |
| 166 | C₆H₅—CO— | —CO— | —C(CH₃)₃ | 207–210 |
| 167 | H | —CO— | —OCH₃ | 223 decomposition |
| 168 | (CH₃CH₂)₂N— | —CO— | phenyl | 128–132 |
| 169 | C₆H₅—C(O)—O—CH₂— | —CO— | phenyl | 221–222 |
| 170 | H | —CO— | phenyl | 198–201 |
| 171 | phenyl | —SO₂— | 4-(NHCOCH₃)phenyl | 151–154 |
| 172 | C₆H₅—CH₂— | —SO₂— | 4-CH₃-phenyl | 120–124 |
| 173 | cyclohexyl (H) | —SO₂— | 4-CH₃-phenyl | 186–190 |
| 174 | H₃C—(H₂C)₁₀— | —SO₂— | 4-CH₃-phenyl | 73–76 |
| 175 | H₃C—(H₂C)₃— | —SO₂— | 4-CH₃-phenyl | 123–126 |
| 176 | 1-Adamantyl- | —SO₂— | 4-CH₃-phenyl | 228–236 |

TABLE 1-continued

| No. | R | —Z— | M | Melting point °C. |
|---|---|---|---|---|
| 177 | (H₃C)₂—HC— | —SO₂— | —⟨C₆H₄⟩—CH₃ | 123–125 |
| 178 | H₃C—(H₂C)₃— | —SO₂— | —CH₃ | 90–93 |
| 179 | ⟨thiophene⟩ | —SO₂— | —⟨C₆H₄⟩—CH₃ | 199–202 |
| 180 | (CH₃)₂CH—O— | —SO₂— | —⟨C₆H₄⟩—CH₃ | 152–155 |
| 181 | ⟨C₆H₅⟩— | —SO₂— | —⟨C₆H₄⟩—Cl | 215–217 |
| 182 | CH₃—O— | —SO₂— | —⟨C₆H₄⟩—Cl | 170–172 |
| 183 | ⟨C₆H₅⟩— | —SO₂— | —⟨C₆H₄⟩—CH₃ | 210–212 |
| 184 | CH₃S— | —SO₂— | —⟨C₆H₄⟩—CH₃ | 172–174 |
| 185 | Br— | —SO₂— | —⟨C₆H₄⟩—CH₃ | 149–153 |
| 186 | H— | —SO₂— | —⟨C₆H₄⟩—CH₃ | 170–176 |

EXAMPLE 1

α-[3-(2-Benzoylimino-5-phenyl-1,3,4-thiadiazolinyl]-α-pivalyl-2-chloro-5-[γ-(2,4-di-t-amylphenoxy)-butyramino]-acetanilide A mixture of 351 mg (1.1 mmols) of the potassium salt of 2-benzoylamino-5-phenyl-1,3,4-thiadiazole and 650 mg (1 mmol) of α-pivalyl-α-bromo-2-chloro-5-[γ-(2,4-di-t-amylphenoxy)-butyramino]-acetanilide is stirred in 15 ml of absolute acetonitrile for 3 hours at room temperature. The yellow suspension is poured into 250 ml of water, the pH of which has previously been adjusted to 2.5 with 2 N hydrochloric acid. The white precipitate is filtered off, washed with a little water and recrystallised from ethanol. This gives 480 mg of the acetanilide of the formula

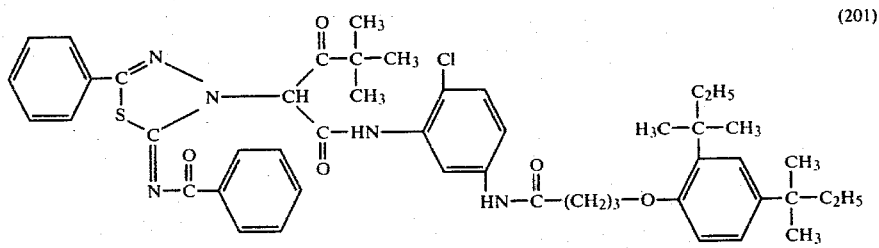

(201)

with a melting point of 127° to 131° C.
D$_{max}$: 1.40 (compare Example 7).

EXAMPLE 2

In the manner described in Example 1, the potassium salt of 2-benzoylamin-5-methoxy-1,3,4-thiadiazole is reacted with the acetanilide of the indicated composition. The product of the formula

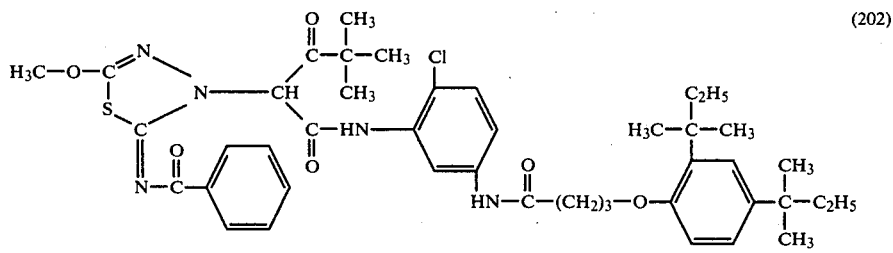
(202)

which is thus obtained, melts at 149° to 150° C.
$D_{max}$: 1.66.

$D_{max}$: 1.66.
The other compounds of the formula

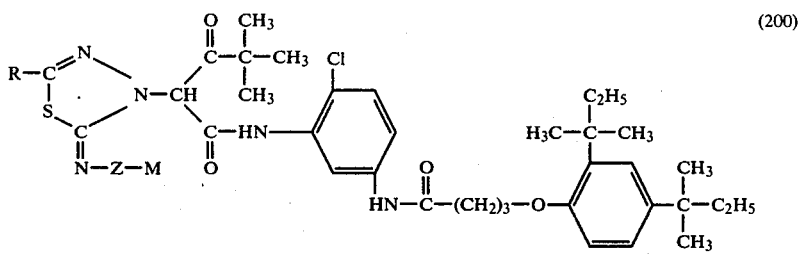
(200)

EXAMPLE 3

In the manner described in Example 1, the potassium salt of 2-p-toluenesulphonylamino-5-methoxy-1,3,4-thiadiazole is reacted with the same acetanilide. This gives a product which melts at 150° C. to 152° C. with decomposition and corresponds to the formula indicated in Table II which follows can also be manufactured in an analogous manner.

At the same time, the maximum density $D_{max}$ at the absorption maximum (442–444 nm) is given for the yellow dyestuffs obtained from the yellow couplers after exposure and photographic development (according to Example 7).

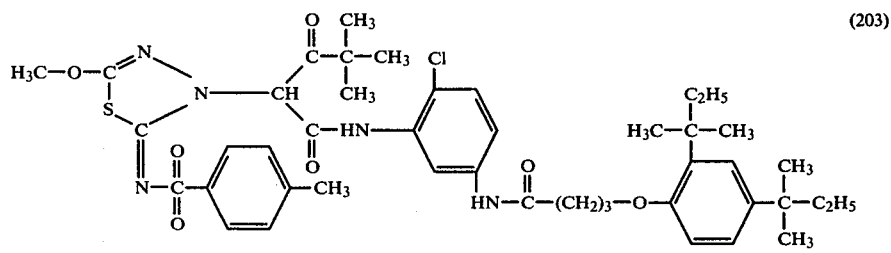
(203)

TABLE II

| No. | R— | —Z— | —M | Melting point, °C. | $D_{max}$ |
|---|---|---|---|---|---|
| 204 | H— | —CO— | —CH₃ | 94–103 | 1.38 |
| 205 | H₃C— | —CO— | —CH₃ | 92–97 | 1.45 |
| 206 | H— | —CO— | —C₂H₅ | 92–98 | 1.21 |
| 207 | H₃C— | —CO— | —H₂C—⌬ | 176–180 | 1.52 |
| 208 | H₃C— | —CO— | —⌬ | 166–167 | 1.59 |
| 209 | H₃C— | —CO— | —(CH₂)₁₂—CH₃ | 141–142 | 1.16 |
| 210 | H₃C— | —CO— | —⌬—NO₂ | 151–153 | 1.15 |
| 211 | H₃C— | —CO— | —⌬—Cl | 132–134 | 1.35 |
| 212 | H₃C—S— | —CO— | —CH₃ | 110–112 | 1.45 |
| 213 | ⌬—H₂C— | —CO— | —CH₃ | 98–102 | 1.38 |
| 214 | H₃C— | —CO— | —⌬—CH₃ | 140–143 | 1.30 |
| 215 | H₃C— | —CO— | —CCl₃ | 183–186 | 1.43 |

TABLE II-continued

| No. | R— | —Z— | —M | Melting point, °C. | $D_{max}$ |
|---|---|---|---|---|---|
| 216 | phenyl | —CO— | 4-C(CH₃)₃-phenyl | 183–188 | 1.36 |
| 217 | phenyl | —CO— | 3-CH₃-phenyl | 101–114 | 1.27 |
| 218 | phenyl | —CO— | 4-OCH₃-phenyl | 110–125 | 1.39 |
| 219 | phenyl | —CO— | 3,4-di(OCH₃)-phenyl | 178–180 | 1.37 |
| 220 | phenyl | —CO— | 3,4,5-tri(OCH₃)-phenyl | 174–177 | 1.40 |
| 221 | phenyl | —CO— | 3,4-di-Cl-phenyl | 160–161 | 1.21 |
| 222 | Cl— | —CO— | phenyl | 164–165 | 1.45 |
| 223 | phenyl | —CO— | —C(CH₃)₃ | 95–99 | 1.51 |
| 224 | phenyl | —CO— | —CH₂—O—[2,4-di(3-ethyl-3-methylpentan-3-yl)phenyl] | 100–107 | 1.44 |
| 225 | phenyl | —CO— | —CH₂Cl | 149–150 | 1.39 |
| 226 | phenyl | —CO— | 2-Cl-phenyl | 139–141 | 1.21 |
| 227 | H₃C—S— | —CO— | phenyl | 98–106 | 1.39 |
| 228 | phenyl-H₂C— | —CO— | phenyl | 118–121 | 1.20 |
| 229 | H₃C—(H₂C)₃— | —CO— | phenyl | 151–153 | 1.39 |
| 230 | H₃C—(H₂C)₆— | —CO— | phenyl | 153–155 | 1.12 |
| 231 | (H₃C)₂—HC— | —CO— | phenyl | 148–150 | 1.51 |
| 232 | H₃C—(H₂C)₁₀— | —CO— | phenyl | 163–165 | 1.43 |
| 233 | cyclohexyl | —CO— | phenyl | 149–153 | 1.26 |
| 234 | 1-Adamantyl— | —CO— | phenyl | 157–159 | 1.41 |
| 235 | (H₃C)₃C— | —CO— | phenyl | 121–124 | 1.31 |
| 236 | phenyl-H₂C— | —CO— | —(CH₂)₆—CH₃ | 83–85 | 1.32 |
| 237 | H₃C—(H₂C)₆— | —CO— | —C(CH₃)₃ | 130–132 | 1.37 |
| 238 | (H₃C)₃C— | —CO— | —C(CH₃)₃ | 157–159 | 1.41 |
| 239 | H₃C—(H₂C)₁₀— | —CO— | —C(CH₃)₃ | 152–154 | 1.33 |

TABLE II-continued

| No. | R— | —Z— | —M | Melting point, °C. | $D_{max}$ |
|---|---|---|---|---|---|
| 240 | C₆H₅—H₂C— | —CO— | —C(CH₃)₃ | 98–103 | 1.36 |
| 241 | H₃C—(H₂C)₃— | —CO— | —C(CH₃)₃ | 125,5–128 | 1.32 |
| 242 | C₆H₅— | —CO— | —(CH₂)₃CH₃ | 189–191 | 1.48 |
| 243 | H₃C—(H₂C)₃— | —CO— | —(CH₂)₃CH₃ | 183–185 | 1.36 |
| 244 | H₃C—(H₂C)₃— | —CO— | —CCl₃ | 151–153 | 1.38 |
| 245 | (H₃C)₂—HC—H₂C— | —CO— | —CCl₃ | 193–196 | 1.47 |
| 246 | C₆H₅—H₂C— | —CO— | —N(CH₃)₂ | 118–121 | 1.30 |
| 247 | H₃C—(H₂C)₃— | —CO— | —NH—C₆H₅ | 134–136 | 1.26 |
| 248 | (H₃C)₂—HC— | —CO— | —(CH₂)₃—O—[2,4-di(1,1-dimethylpropyl)phenyl] | 174–176 | 1.29 |
| 249 | (H₃C)₃C— | —CO— | —(CH₂)₃—O—[2,4-di(1,1-dimethylpropyl)phenyl] | 159–162 | 1.48 |
| 250 | C₆H₅— | —CO— | 3-pyridyl | 126–127 | 1.24 |
| 251 | 2-thienyl | —CO— | —C(CH₃)₃ | 185–186 | 1.52 |
| 252 | C₆H₅— | —CO— | —O—CH₂—CH₃ | 176–179 | 1.46 |
| 253 | (CH₃)₂CH—S— | —CO— | —OCH₂CH₃ | 82–83 | 1.50 |
| 254 | CH₃—S— | —CO— | —OCH₂CH₃ | 154–155 | 1.39 |
| 255 | (CH₃)₂CH—S— | —CO— | —C(CH₃)₃ | 75–85 | 1.35 |
| 256 | CH₃CH₂—S— | —CO— | C₆H₅— | 93–97 | 1.39 |
| 257 | (CH₃)₂CH—S— | —CO— | C₆H₅— | 140–141 | 1.56 |
| 258 | (CH₃)₂N—SO₂— | —CO— | —CH₃ | 160–163 | 1.36 |
| 259 | (CH₃)₂CH—O— | —CO— | C₆H₅— | 137–140 | 1.28 |
| 260 | CH₃O— | —CO— | —C(CH₃)₃ | 116–118 | 1.32 |
| 261 | CH₃S— | —CO— | —C(CH₃)₃ | 139–141 | 1.59 |
| 262 | CH₃S— | —CO— | —CH₂OCH₂CH₃ | 102–106 | 1.49 |
| 263 | C₆H₅— | —CO— | 2,4-dichlorophenyl | 178–182 | 1.33 |

TABLE II-continued

| No. | R— | —Z— | —M | Melting point, °C. | $D_{max}$ |
|---|---|---|---|---|---|
| 264 | C₆H₅—C(=O)— | —CO— | —C₆H₅ | 115–118 | 1.41 |
| 265 | (CH₃)₂CH—CH₂— | —CO— | —OCH₃ | 162–165 | 1.43 |
| 266 | C₆H₅—C(=O)— | —CO— | —C(CH₃)₃ | 90–93 | 1.52 |
| 267 | H— | —CO— | —OCH₃ | 99–102 | 1.51 |
| 268 | (CH₃—CH₂)₂N— | —CO— | —C₆H₅ | 136–139 | 1.38 |
| 269 | C₆H₅—C(=O)—O—CH₂— | —CO— | —C₆H₅ | 114–120 | 1.17 |
| 270 | H— | —CO— | —C₆H₅ | 125–128 | 1.49 |
| 271 | C₆H₅— | —SO₂— | —C₆H₄—NH—OC—CH₃ | 135–139 | 1.22 |
| 272 | C₆H₅—H₂C— | —SO₂— | —C₆H₄—CH₃ | 183–185 | 1.30 |
| 273 | cyclo-C₆H₁₁— | —SO₂— | —C₆H₄—CH₃ | 190–192 | 1.34 |
| 274 | H₃C—(H₂C)₁₀— | —SO₂— | —C₆H₄—CH₃ | 121–123 | 1.33 |
| 275 | H₃C—(H₂C)₃— | —SO₂— | —C₆H₄—CH₃ | 172–174 | 1.21 |
| 276 | 1-Adamantyl | —SO₂— | —C₆H₄—CH₃ | 217–220 | 1.34 |
| 277 | (H₃C)₂ | —SO₂— | —C₆H₄—CH₃ | 168–169 | 1.45 |
| 278 | H₃C—(H₂C)₃— | —SO₂— | —CH₃ | 212–213 | 1.31 |
| 279 | 2-thienyl | —SO₂— | —C₆H₄—CH₃ | 197–198 | 1.49 |
| 280 | (CH₃)₂CH—O— | —SO₂— | —C₆H₄—CH₃ | 181–184 | 1.42 |
| 281 | C₆H₅— | —SO₂— | —C₆H₄—Cl | 194–196 | 1.30 |
| 282 | CH₃—O— | —SO₂— | —C₆H₄—Cl | 179–181 | 1.58 |
| 283 | C₆H₅— | —SO₂— | —C₆H₄—CH₃ | 192–193 | 1.32 |
| 284 | CH₃S— | —SO₂— | —C₆H₄—CH₃ | 144–147 | 1.45 |
| 285 | Br— | —SO₂— | —C₆H₄—CH₃ | 73–76 | 1.18 |
| 286 | H— | —SO₂— | —C₆H₄—CH₃ | 128–130 | 1.56 |

EXAMPLE 4

2.1 g of α-chloro-α-{3-[γ-(2,4di-tert.-pentyl-phenoxy)-butyramino]-benzoyl}-4-chloro-2,5-dimethoxy-acetanilide, 1.3 g of 2-isopropyl-5-p-toluenesulphonimido-4H-1,3,4-thiadiazoline and 300 mg of pulverulent potassium hydroxide are stirred in 30 ml of acetonitrile for 5 hours at room temperature. The residue obtained after distilling off the solvent is chromatographed on 60 g of silica gel and the residue from the pure fractions is recrystallised from 1:3:8 benzene/ether/hexane.

This gives the coupler of the formula

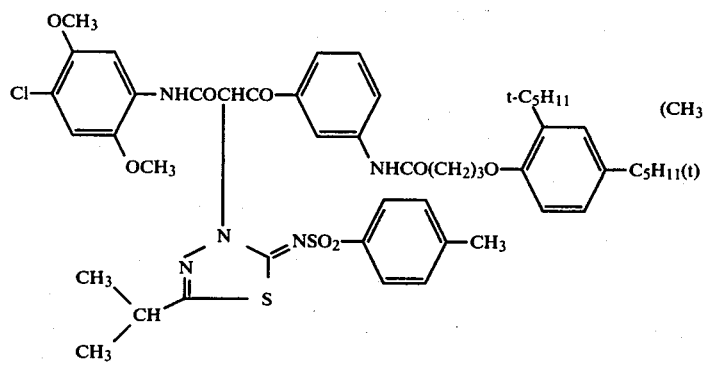

in the form of a white powder with a melting point of 110°–112° C.

D$_{max}$: 1.85

The further compounds of the formulae

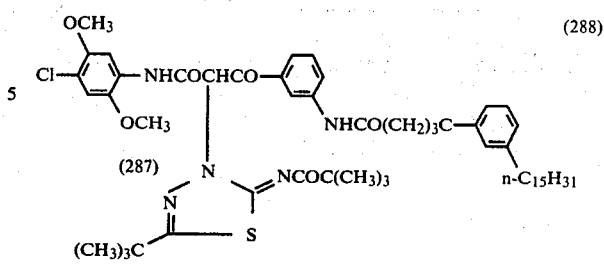
(287)(288)

Melting point: 55° C.
D$_{max}$: 1.59

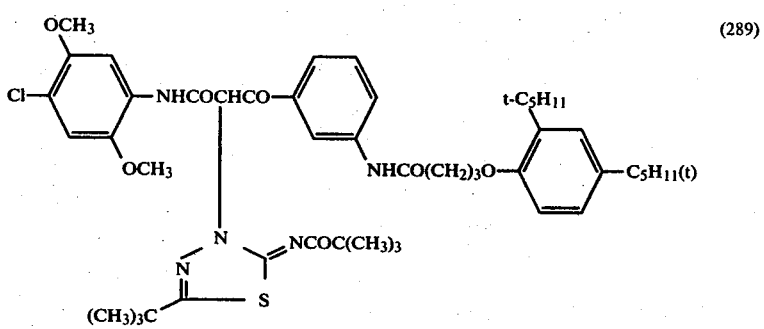
(289)

Melting point: 85°–90° C.
D$_{max}$: 1.26 and

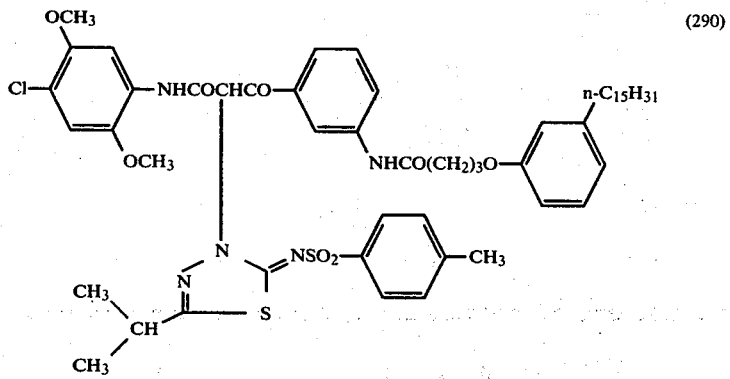
(290)

Melting point: 65° to 70° C.
D$_{max}$: 1.64 are obtained in an analogous manner.

EXAMPLE 5

9.6 g of α-chloro-α-pivalyl-2-chloro-5-n-dodecyloxycarbonyl-acetanilide and 2.88 g of the potassium salt of 2-isopropyl-5-p-toluene-sulphonimido-1,3,4-thiadiazoline are stirred in 80 ml of ethyl acetate for 3 hours at room temperature. The resulting crude product is recrystallised three times from ether/hexane.

This gives the coupler of the formula

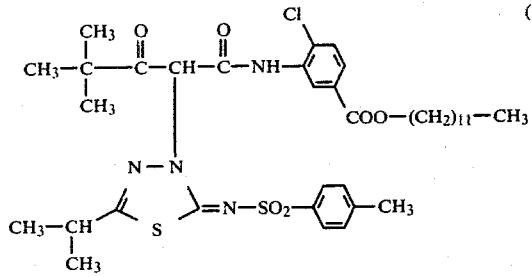
(291)

with a melting point of 48°–52° C.
$D_{max}$: 1.48

The couplers of the following formulae:

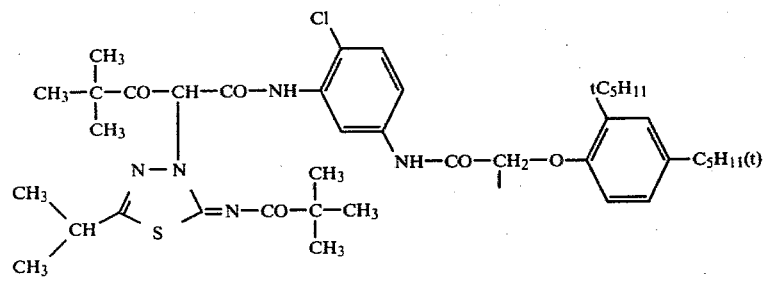
(292)

Melting point: 70°–73° C.
$D_{max}$: 1.28

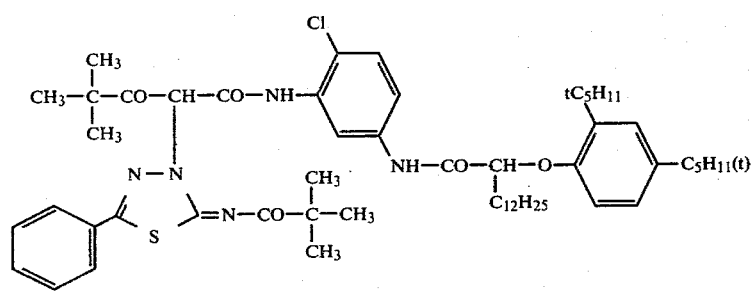
(293)

Melting point: 49°–52° C.
$D_{max}$: 1.17

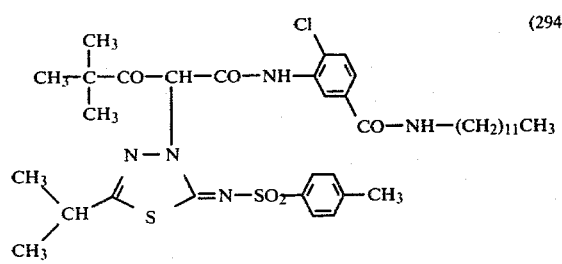
(294)

Melting point: 79°–81° C.
$D_{max}$: 1.20

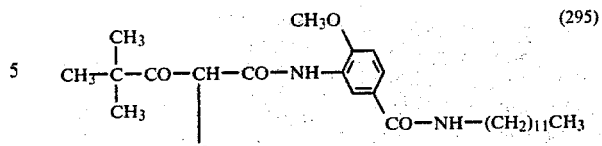
(295)

Melting point: 61°–65° C.
$D_{max}$: 1.19

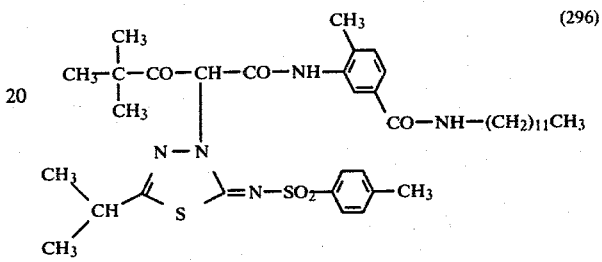
(296)

Melting point: 79°–81° C.
$D_{max}$: 1.20 and

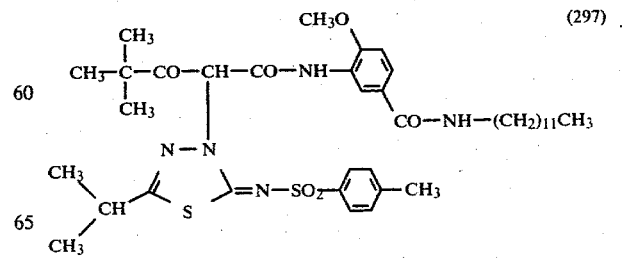
(297)

Melting point: 61°–65° C.

$D_{max}$: 1.19 are obtained in an analogous manner.

EXAMPLE 6

6.5 g of α-bromo-α-pivalyl-2-chloro-5-[γ-(2,4-di-t-amyl-phenoxy)-butyramino]-acetanilide, 2.1 g of bis-[N,N'-5-t-butyl-1,3,4-thiadiazolyl-2-]-adipic acid diamide and 2.0 g of potassium carbonate are stirred in 70 ml of tridimethylaminophosphine oxide for 3 days at room temperature. The yellow solution is poured into 200 ml of water and extracted with chloroform and the chloroform phase is washed several times with 2 N hydrochloric acid and evaporated. The oil formed is chromatographed on silica gel using 1:4 ethyl acetate/petroleum ether. This gives 1.2 g of the acetanilide of the formula

EXAMPLE 7

0.1 mmol of the yellow coupler of the formula (201), the preparation of which is described in Example 1, is dissolved in 2.0 ml of tricresyl phosphate/methylene chloride (1:9). The methylene chloride is evaporated off, 2.0 ml of an 8% strength aqueous solution of sodium isopropylnaphthalenesulphonate, 6.6 ml of 6% strength gelatine solution and 1.2 ml of water are added, the pH of the mixture is adjusted to 6.5 and the mixture is emulsified for 5 minutes with the aid of an ultrasonic device with an output of 100 watts.

2.5 ml of the coupler emulsion, freshly exposed to ultrasonic waves, 1.6 ml of silver bromide emulsion which has a pH of 6.5 and contains 1.4% of silver and

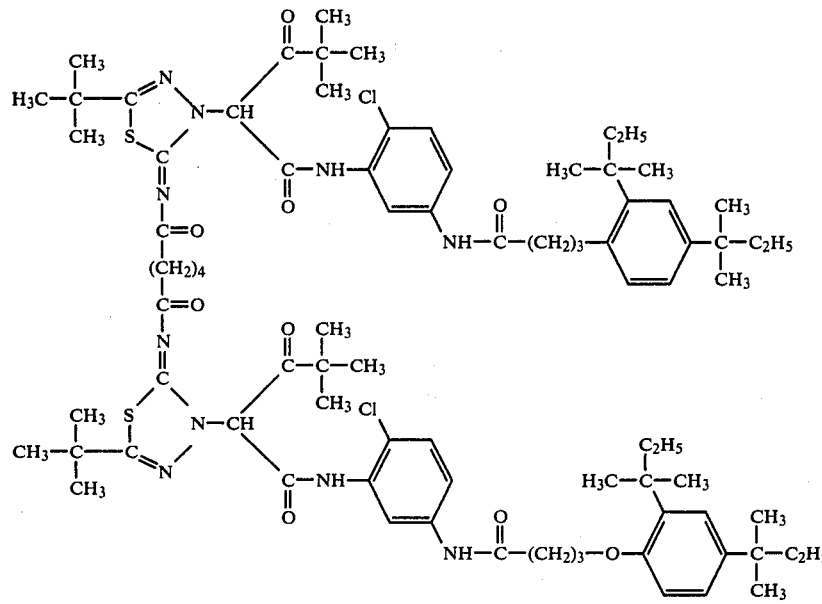

(298)

$\lambda_{max}=442$ nm, $D_{max}=1.45$ (compare Example 7 for the determination of $D_{max}$).

In addition, 1.5 g of the acetanilide of the formula 6.0% of gelatine, 1.0 ml of a 1% strength aqueous solution of the hardener of the formula

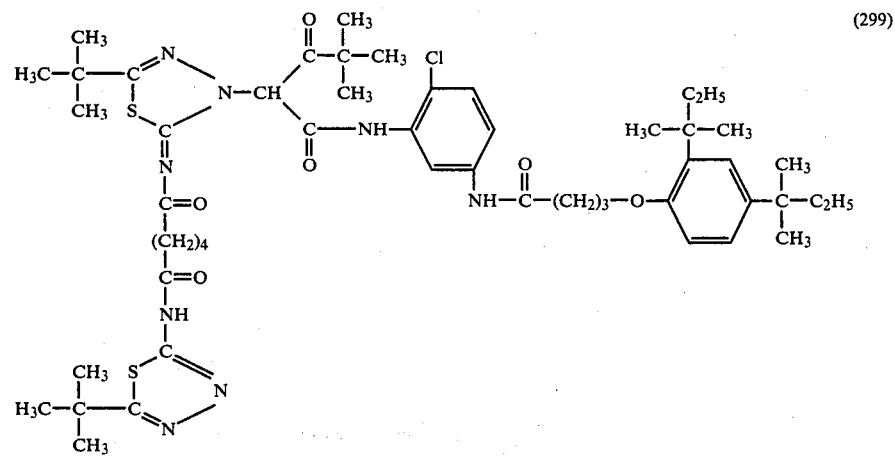

(299)

are obtained.
Melting point: 154°–156° C.

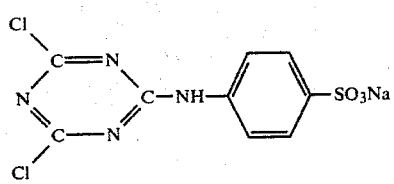

and 5.0 ml of water are mixed together and coated, at 40° C., onto a subbed 13 cm×18 cm glass plate.

After the mixture has solidified at 10° C., the plate is dried in a circulating air drying cabinet at room temperature.

A strip cut to 4.0 cm×6.5 cm is exposed, at 500 lux, under a step wedge for 2 seconds and then treated at 24° C. in the following way:

| | | Minutes |
|---|---|---|
| 1. | Colour development | 5 |
| 2. | Washing | 5 |
| 3. | First fixing | 2 |
| 4. | Washing | 2 |
| 5. | Silver bleaching | 4 |
| 6. | Washing | 2 |
| 7. | Second fixing | 4 |
| 8. | Washing | 10 |
| 9. | Drying | 10 |

Colour developers of the following compositions can be used for processing:

| | |
|---|---|
| (a) 4-Amino-3-methyl-N-ethyl-N-[β-(methyl-sulphonamido)-ethyl]-aniline . 1½ H$_2$SO$_4$ . H$_2$O | 10 mmols/l |
| Anhydrous sodium sulphite | 2.0 g/l |
| Potassium bromide | 0.5 g/l |
| Potassium carbonate | 40.0 g/l |
| Benzyl alcohol | 10.0 ml/l |
| (pH: 10.7) | |
| or | |
| (b) 4-Amino-3-methyl-N-ethyl-N-[β-(methyl sulphonamido)-ethyl]-aniline . 1½ H$_2$SO$_4$ . H$_2$O | mmols/l |
| Anhydrous sodium sulphite | 2.0 g/l |
| Potassium bromide | 0.5 g/l |
| Potassium carbonate | 40.0 g/l |
| (pH: 10.7) | |

Conventional baths are used for fixing and silver bleaching.

A clear, sharp yellow wedge which has an absorption maximum at 444 nm and a maximum density D$_{max}$ of 1.40, is obtained in the manner described above.

EXAMPLE 8 (COMPARISON EXAMPLE)

The procedure according to the instructions of Example 7 is followed, using the known colour couplers which follow. The yellow dyestuffs formed in general display a lower colour density at the absorption maximum than the yellow dyestuffs which are formed from the yellow couplers according to the invention.

(a) German Offenlegungsschrift No. 2,057,941, coupler (1).

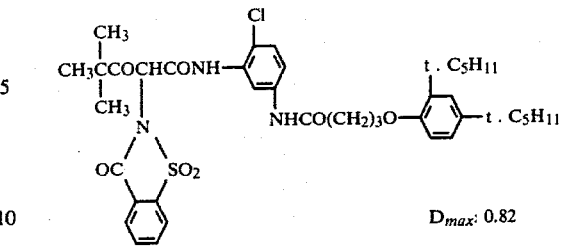

D$_{max}$: 0.82

(b) German Offenlegungsschrift No. 2,261,361, coupler (29)

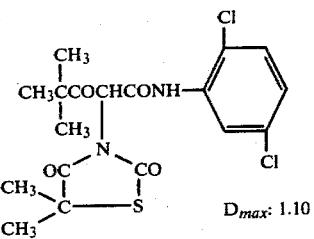

D$_{max}$: 1.10

(c) German Offenlegungsschrift No. 2,431,480, coupler (43)

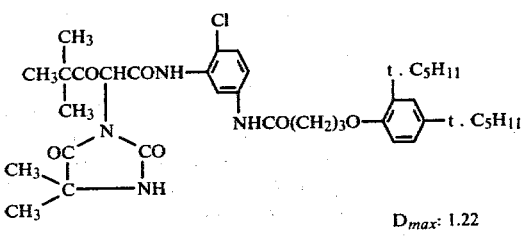

D$_{max}$: 1.22

(d) German Offenlegungsschrift No. 2,528,638, coupler (1)

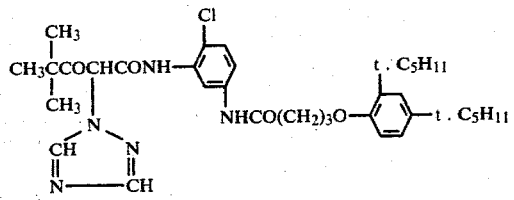

D$_{max}$: 1.09 and
(e) German Offenlegungsschrift No. 2,528,638, coupler (17)

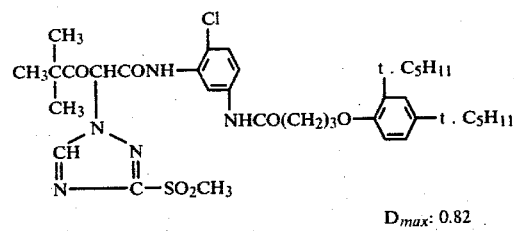

D$_{max}$: 0.82

What is claimed is:

1. A yellow coupler which corresponds to the formula

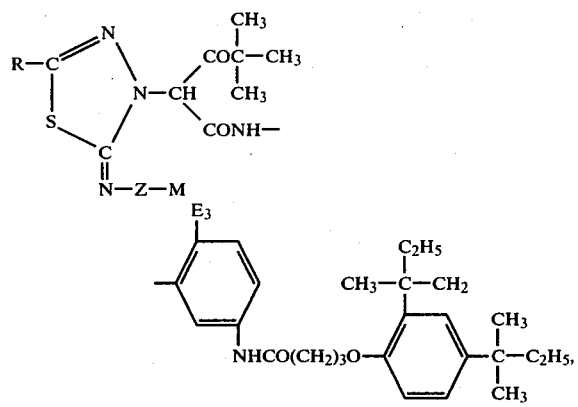

in which $E_3$ is chlorine or alkyl or alkoxy with 1 to 4 carbon atoms, M is alkyl with 1 to 13 carbon atoms, optionally substituted by halogen, alkoxy with 1 to 5 carbon atoms or phenoxy optionally substituted by alkyl with 1 to 5 carbon atoms; alkoxy with 1 to 5 carbon atoms; benzyl, cyclohexyl or 1-adamantyl, phenyl or phenyl substituted by alkyl or alkoxy with 1 to 5 carbon atoms, halogen, nitro or $-NHCOC_nH_{2n+1}$, in which n is 1 to 5; pyridyl, phenylamino of dialkylamino with, in each case, 1 to 5 carbon atoms in the alkyl part, R is hydrogen, alkyl with 1 to 12 carbon atoms, benzyl, phenyl, thienyl, cyclohexyl or 1-adamantyl, alkoxy with 1 to 5 carbon atoms, alkylmercapto with 1 to 4 carbon atoms, halogen, benzoyl, benzoyloxyalkyl with 1 to 5 carbon atoms in the alkyl part, benzoylamino, mono- or dialkylamino with 1 to 5 carbon atoms in the alkyl part, $SO_2NH_2$, N,N-dialkylsulphonamide with, in each case, 1 to 5 carbon atoms in the alkyl part, or $-NHCOC_nH_{2n+1}$, in which n is 1 to 5, and Z is $-CO-$ or $-SO_2-$.

2. A yellow coupler according to claim 1, which corresponds to the formula

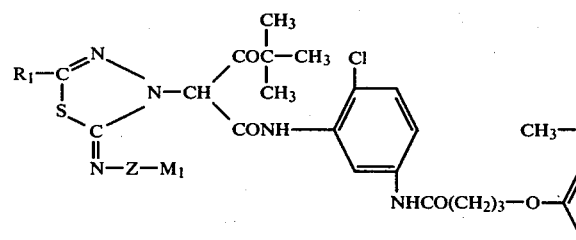

in which $M_1$ is alkyl with 1 to 13 carbon atoms, optionally substituted by halogen, alkoxy with 1 to 5 carbon atoms; or phenoxy optionally substituted by alkyl with 1 to 5 carbon atoms; alkoxy with 1 to 5 carbon atoms; benzyl, cyclohexyl or 1-adamantyl, phenyl or phenyl substituted by alkyl or alkoxy with 1 to 5 carbon atoms, halogen, nitro or $-NHCOC_nH_{2n+1}$, in which n is 1 to 5; pyridyl, phenylamino or dialkylamino with, in each case, 1 to 5 carbon atoms in the alkyl part, $R_1$ is hydrogen, alkyl with 1 to 12 carbon atoms, benzyl, phenyl, thienyl, cyclohexyl or 1-adamantyl, alkoxy with 1 to 5 carbon atoms, alkylmercapto with 1 to 4 carbon atoms, halogen, benzoyl, benzoyloxyalkyl with 1 to 5 carbon atoms in the alkyl part, benzoylamino, mono- or dialkylamino with 1 to 5 carbon atoms in the alkyl part, $SO_2NH_2$, N,N-dialkylsulphonamide with, in each case, 1 to 5 carbon atoms in the alkyl part, or $-NHCOC_nH_{2n+1}$, in which n is 1 to 5, and Z is $-CO-$ or $-SO_2-$.

3. A yellow coupler according to claim 2, which corresponds to the formula

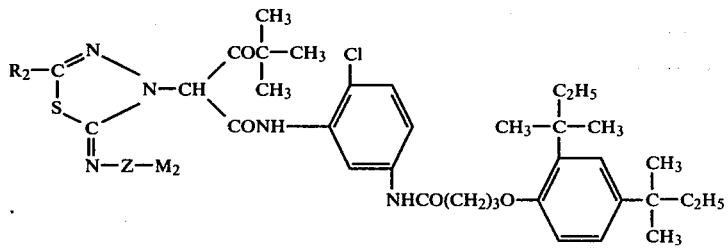

in which $M_2$ is straight-chain or branched alkyl with 1 to 7 carbon atoms, $-CH_2Cl$, $-CCl_3$, $-CH_2OC_2H_5$ $-CH_2O-\underset{t\text{-Amyl}}{\underset{|}{\text{Ph}}}-t\text{-Amyl}, \quad -(CH_2)_3O-\underset{t\text{-Amyl}}{\underset{|}{\text{Ph}}}-t\text{-Amyl},$ alkoxy with 1 or 2 carbon atoms, benzyl, phenyl, tolyl, t-butylphenyl, methoxyphenyl, dimethoxyphenyl, chlorophenyl, dichlorophenyl, nitrophenyl, acetylaminophenyl, pyridyl, anilino or dimethylamino, $R_2$ is hydrogen, alkyl with 1 to 12 carbon atoms, phenyl, benzyl, thienyl, cyclohexyl, norbornyl, 1-adamantyl, alkoxy with 1 to 3 carbon atoms, alkylmercapto with 1 to 4 carbon atoms, chlorine, bromine, benzoyl, benzoyloxyalkyl with 1 to 3 carbon atoms in the alkyl part, benzylamino, mono- or dialkylamino with 1 or 2 carbon atoms in the alkyl part, N,N-dialkylsulphonamide with 1 or 2 carbon atoms in the alkyl part, or $-NHCOC_{n_1}H_{2n_1+1}$, in which $n_1$ is 1 or 2, and Z is $-CO-$ or $-SO_2-$.

4. A yellow coupler according to claim 3, wherein $R_2$ is hydrogen, alkyl with 1 to 12 carbon atoms, phenyl, benzyl, thienyl, cyclohexyl, 1-adamantyl, methoxy, ethoxy, propoxy, methylmercapto, propylmercapto, chlorine, bromine, benzoyl, benzoyloxymethyl, benzylamino, methylamino, diethylamino, —SO₂N(CH₃)₂ or —NHCOCH₃ and M₂ has the meaning indicated in claim 3.

in which M₃ is methyl, t-butyl, p-tolyl, p-chlorophenyl or p-acetylaminophenyl and R₃ is hydrogen, alkyl with 1 to 10 carbon atoms, cyclohexyl, 1-adamantyl, methoxy, i-propoxy, methylmercapto, chlorine, bromine, phenyl, benzyl or thienyl.

6. A compound of the formula

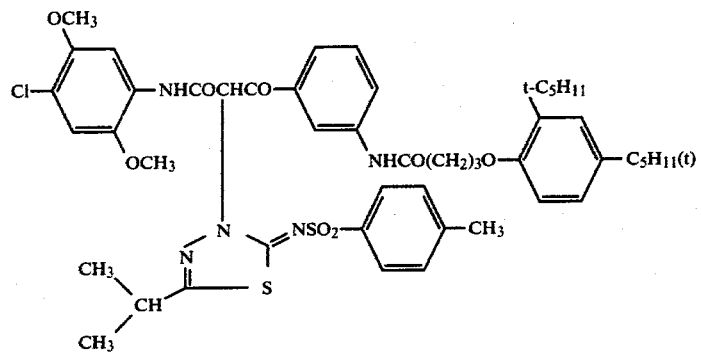

5. A yellow coupler according to claim 4, which corresponds to the formula

7. A compound of the formula

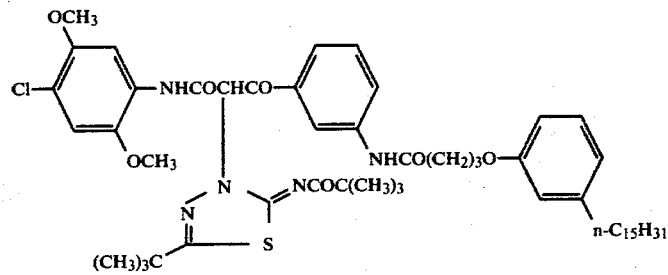

8. A compound of the formula (8)

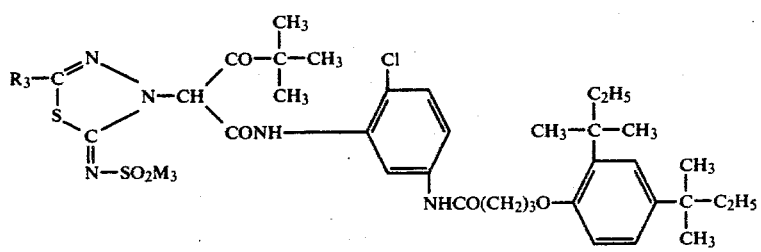

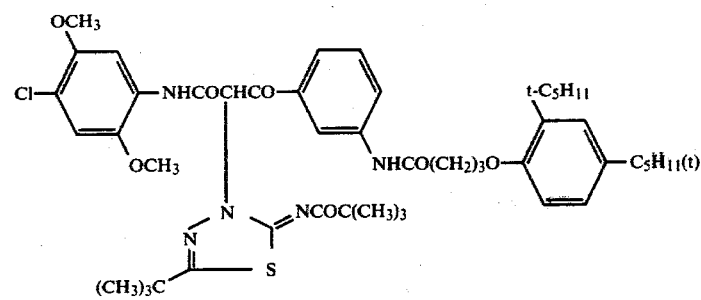

9. A compound of the formula

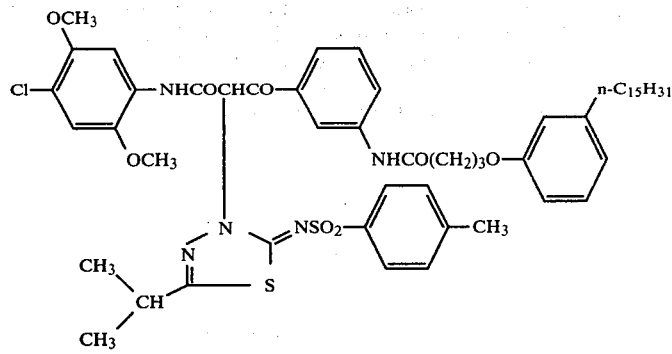
10. A compound of the formula
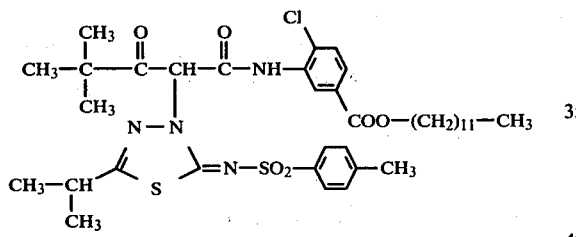
11. A compound of the formula
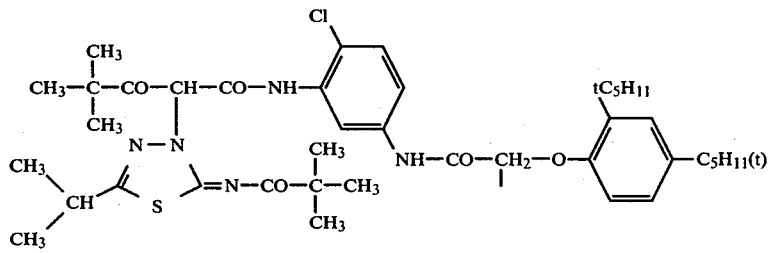
12. A compound of the formula
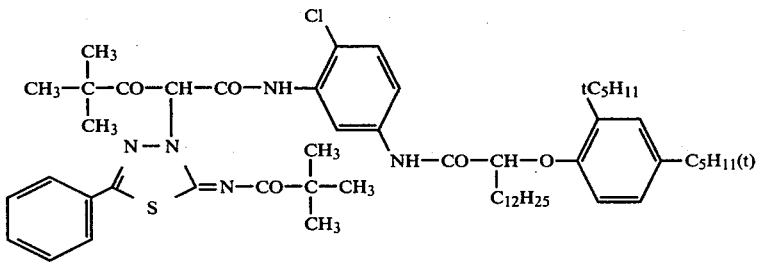
13. A compound of the formula
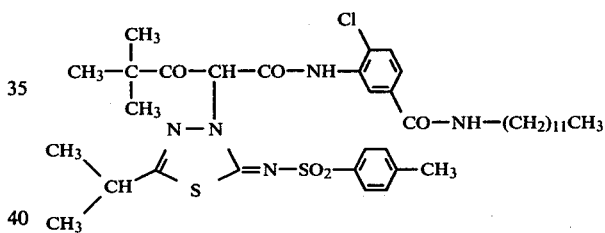
* * * * *

UNITED STATES PATENT AND TRADEMARK OFFICE
CERTIFICATE OF CORRECTION

PATENT NO. : 4,229,577
DATED : October 21, 1980
INVENTOR(S) : Graham Evans, et al.

It is certified that error appears in the above—identified patent and that said Letters Patent is hereby corrected as shown below:

Title Page, Rel, U.S. Appl. Data, "Mar. 20" should be "Mar. 30".

Column 3, line 57, "carboxyic" should be "carboxylic".

Column 14, line 59, "$\alpha$($\beta$'" should be "$\alpha$-($\beta$'".

Column 14, line 59, "$\alpha,\alpha$'" should be "$\alpha',\alpha'$".

Column 14, lines 66-67, delete 2 lines.

Column 26, line 65, "benzoylamin" should be "benzoylamino".

Column 33, line 66, "2,4 di-" should be "2,4-di-".

Column 43, line 40, "of" should be "or".

Signed and Sealed this

Twenty-first Day of April 1981

[SEAL]

Attest:

RENE D. TEGTMEYER

Attesting Officer  Acting Commissioner of Patents and Trademarks